US012567483B2

(12) United States Patent
Bilal et al.

(10) Patent No.: US 12,567,483 B2
(45) Date of Patent: Mar. 3, 2026

(54) AUTOMATED LABELING OF USER SENSOR DATA

(71) Applicant: INTERNATIONAL BUSINESS MACHINES CORPORATION, Armonk, NY (US)

(72) Inventors: Erhan Bilal, Westport, CT (US); Tian Hao, White Plains, NY (US); Bing Dang, Chappaqua, NY (US); Bo Wen, New York, NY (US); Jeffrey L. Rogers, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 249 days.

(21) Appl. No.: 18/059,570

(22) Filed: Nov. 29, 2022

(65) Prior Publication Data

US 2024/0177815 A1 May 30, 2024

(51) Int. Cl.
*G16H 10/60* (2018.01)

(52) U.S. Cl.
CPC .................................... *G16H 10/60* (2018.01)

(58) Field of Classification Search
None
See application file for complete search history.

(56) References Cited

U.S. PATENT DOCUMENTS 8,989,053 B1 * 3/2015 Skaaksrud .............. H04W 4/80
370/255
2009/0326982 A1 * 12/2009 Deobhakta ............. G16H 10/60
705/3

2013/0073302 A1 * 3/2013 Ryan ....................... G16H 40/20
705/2
2013/0096731 A1 * 4/2013 Tamari ................ G06F 11/3058
701/1
2013/0325508 A1 * 12/2013 Johnson ................. G16H 10/60
705/3
2015/0106020 A1 4/2015 Chung
2016/0317077 A1 11/2016 Sillay
2018/0246570 A1 8/2018 Coleman
2018/0288024 A1 * 10/2018 Munafo ................ G16H 40/67
2020/0376335 A1 12/2020 Wan
2021/0232860 A1 * 7/2021 Liu ........................ G06F 18/214
2022/0172841 A1 * 6/2022 Steinberg-Koch ..... G16H 50/70
(Continued)

FOREIGN PATENT DOCUMENTS

TW 526976 B 6/2015

OTHER PUBLICATIONS

Liang et al., "Combining Resampling and Machine Learning to Improve Sleep-Wake Detection of Fitbit Wristbands," 2019, 2019 IEEE International Conference, on Healthcare Informatics (ICHI), pp. 1-3.

(Continued)

*Primary Examiner* — John A Pauls
(74) *Attorney, Agent, or Firm* — Scott Dobson

(57) ABSTRACT

Automated labeling of user sensor data is provided. It is determined that a user is at a medical facility using a location of a user device. User sensor data is collected from one or more user devices while the user is at the medical facility. A result is retrieved of a medical evaluation of the user performed at the medical facility. User sensor data collected during the medical evaluation is tagged with the retrieved result from the medical evaluation.

15 Claims, 3 Drawing Sheets

(56)            References Cited

U.S. PATENT DOCUMENTS

| | | | | |
|---|---|---|---|---|
| 2023/0360199 A1* | 11/2023 | Godden | .............. | A61B 5/7275 |
| 2024/0285239 A1* | 8/2024 | Kapur | ................. | A61B 5/7225 |

OTHER PUBLICATIONS

"Cleveland Clinic Studies Accuracy of Apple Watch 4 for Atrial Fibrillation Detection," Feb. 25, 2020, 4 pgs. https://newsroom. clevelandclinic.org/2020/02/25/cleveland-clinic-studies-accuracy-of-apple-watch-4-for-atrial-fibrillation-detection/).

Gan, O.P., "Automatic Labeling for Personalized loT Wearable Monitoring," IECON 2018—44th Annual Conference of the IEEE Industrial Electronics Society, pp. 2861-2866, 2018. https://ieeexplore. ieee.org/document/8592760.

Jaber et al., "Noise reduction of signals received from wearable sensors along with integrating their information with machine learning," Eurasian Journal of Biosciences, vol. 14, No. 2, Oct. 2020, pp. 5253-5259.

Krittanawong et al., "Integration of novel monitoring devices with machine learning technology for scalable cardiovascular management," Nature Reviews Cardiology, Feb. 2021, pp. 75-91, vol. 18.

Liang et al., "Automatic Labeling Framework for Wearable Sensor-based Human Activity Recognition," Sensors and Materials, Jun. 25, 2018, pp. 2049-2052, vol. 30, No. 9. https://myukk.org/SM2017/ sm_pdf/SM1660.pdf.

M. Somrak et al., "Medical diagnostics based on combination of sensor and user-provided data," In AI-AM/NetMed@ECAI, pp. 36-40, Aug. 18, 2014.

M. Somrak et al., "Tricorder: Consumer Medical Device for Discovering Common Medical Conditions," Informatica, 38, pp. 81-88, 2014.

\* cited by examiner

100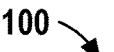

COMPUTER 101

PROCESSOR SET 110

| PROCESSING CIRCUITRY 120 | CACHE 121 |

COMMUNICATION FABRIC 111

VOLATILE MEMORY 112

PERSISTENT STORAGE 113

OPERATING SYSTEM 122

USER SENSOR DATA LABELING MODULE

210

PERIPHERAL DEVICE SET 114

| UI DEVICE SET 123 | STORAGE 124 | IoT SENSOR SET 125 |

NETWORK MODULE 115

WAN 102

END USER DEVICE 103

REMOTE SERVER 104

REMOTE DATABASE 130

PRIVATE CLOUD 106

GATEWAY 140

PUBLIC CLOUD 105

| CLOUD ORCHESTRATION MODULE 141 | HOST PHYSICAL MACHINE SET 142 |
| VIRTUAL MACHINE SET 143 | CONTAINER SET 144 |

AUTOMATED LABELING OF USER SENSOR DATA

BACKGROUND

The present disclosure relates to machine learning, and more specifically, to labeling data sets for training machine learning models.

Machine learning models may be trained using supervised learning algorithms and labeled training data. The algorithms may be configured to learn a function that can be used to predict an output associated with a new input. Many wearable internet of things (IoT) devices are available for purchase by consumers, such as smart watches, rings, and patches, that contain sensors for measuring various health parameters of a user. These consumer devices are often associated with models that output one or more determinations based on input from one or more sensors.

SUMMARY

According to embodiments of the present disclosure, computer-implemented method is provided. The method includes determining that a user is at a medical facility using a location of a user device. User sensor data is collected from one or more user devices while the user is at the medical facility. A result is retrieved of a medical evaluation of the user performed at the medical facility. User sensor data collected during the medical evaluation is tagged with the retrieved result from the medical evaluation.

According to further embodiments of the present disclosure, a system and a computer program product for performing the method are provided.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 1 depicts an example computing environment for user sensor data labeling for machine learning, according to embodiments.

Figure 2:
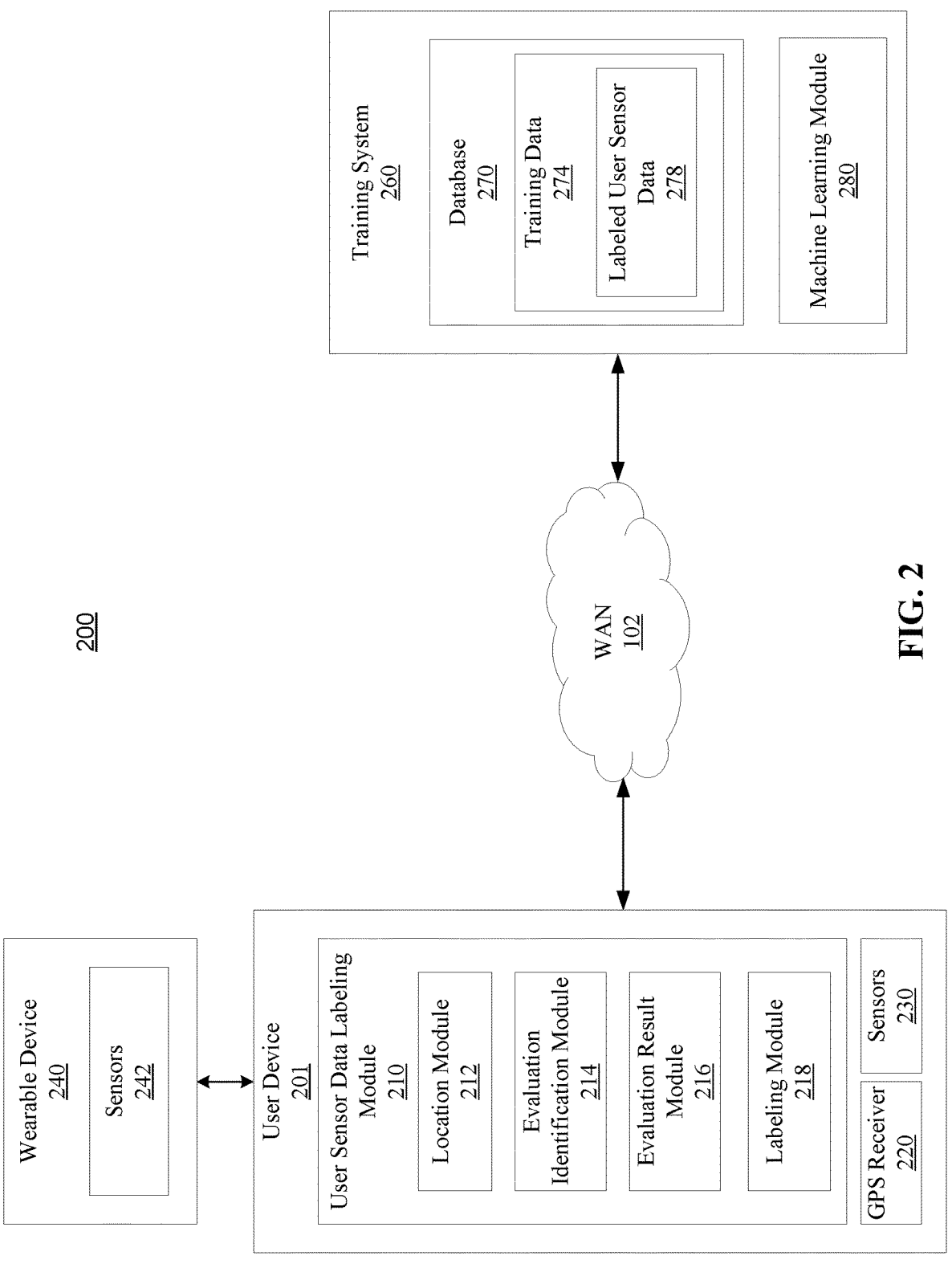
FIG. 2 depicts a second example computing environment for user sensor data labeling for machine learning, according to embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to labeling sensor data for machine learning, and more particular aspects relate to automatically labeling user sensor data with medical evaluation results. While the present disclosure is not necessarily limited to such applications, various aspects of the disclosure may be appreciated through a discussion of various examples using this context.

Many wearable internet of things (IoT) devices are available for purchase by consumers, such as smart watches, rings, and patches, that contain sensors for measuring various health parameters of a user. These consumer devices are often associated with trained models that make one or more determinations based on user sensor data from one or more sensors. For example, a smart watch may measure a user's heart rhythm using electrical heart sensors and determine if there is a potential irregular heart rhythm using the sensor data and a trained model. However, the data from these consumer devices and their associated models are relatively inaccurate when compared to the data and determinations that are made in medical facilities using medical-grade equipment and medical professional evaluation. While some of the inaccuracy is related to the accuracy of the consumer-grade sensors themselves, some of the inaccuracy is due to lack of training data for generating the models due to the cost of obtaining training data through clinical studies. The accuracy of the models used to make determinations based on user sensor data from consumer devices may be improved with more training data.

Embodiments of the present disclosure provide a method, system, and computer program product for automatically labeling sensor data for machine learning. Training data may be identified by determining that a user has been evaluated at a medical facility and labeling the sensor data from the user's commercial devices with one or more results of the medical evaluation.

According to embodiments, the system identifies when a user is located a medical facility using the location of a user device. The location may be determined using any suitable technology such as Global Positioning System (GPS), WiFi positioning, etc. The location of the user may be compared with known locations of medical facilities. As used herein, a medical facility may be any location where a user may receive a medical evaluation such as, for example, hospitals, clinical testing laboratories, medical clinics, pharmacies, etc. The location of the user may be checked continuously, intermittently, or periodically. In some embodiments, the location of the user may be overlayed on a geographic information system (GIS) to determine if the user location corresponds to the location of a medical facility.

In some embodiments, in response to determining that the user is at a medical facility, the system monitors data from the user's devices to identify when a medical evaluation may be taking place. That is, the system may monitor data to determine one or more periods of time when an evaluation is possibly taking place and/or one or more periods of time when an evaluation is unlikely to be taking place. For example, periods of time where the user is walking, as determined using GPS or accelerometer data, may indicate that a user is not undergoing an evaluation at that time. Similarly, when GPS data or accelerometer data indicates that the user is not walking, they may be undergoing an evaluation (e.g., the user may be laying on an examination table undergoing an examination by a medical professional using medical-grade sensors). Further, some evaluations may be associated with particular movements such that user sensor data may be indicate that a particular evaluation is being performed. Captured user sensor data may be compared to one or more profiles containing example sensor data associated with a specific type of evaluation. For example, data from a gyroscope sensor of a user's smartwatch may be used to identify a pronation-supination (PS) test that a user is performing while being assessed by a trained physician.

The system then attempts to retrieve a result from the medical evaluation. The system may retrieve the result, for example, from the user or from the user's electronic medical records. In some embodiments, the system may prompt the user to enter the result of the medical evaluation. For example, the user may be provided with a questionnaire on a graphical user interface of the user's device to confirm that medical evaluations identified using the sensor data were performed and enter corresponding results of the medical evaluations. In some embodiments, the questionnaire may further ask the user to provide information on when the medical evaluations were performed to identify the corresponding user sensor data. In some embodiments, the system may request permission from the user to access the user's electronic medical records. For example, the system may cause a prompt to be displayed on a graphical user interface of the user's device with text including the request to access the user's electronic medical records and one or more selectable user interface objects to allow or deny the request.

In some embodiments, the system may retrieve the result in response to determining that the user has left the medical facility. For example, the system may monitor the user's location, determine that the user is no longer at the medical facility, and, in response, attempt to obtain one or more results from the user or the user's electronic medical records.

Embodiments of the present disclosure may involve the use and storage of user information. Accordingly, embodiments may require the user to opt-in to the use and storage of their personal information. Further, it is contemplated that the use and storage of user information will comply with all applicable laws and regulations.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Computing environment 100 contains an example of an environment for the execution of at least some of the computer code involved in performing the inventive methods, such as user sensor data labeling module 210. In addition to block 210, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 210, as identified above), peripheral device set 114 (including user interface (UI), device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

COMPUTER 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

PROCESSOR SET 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 210 in persistent storage 113.

COMMUNICATION FABRIC 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

VOLATILE MEMORY 112 is any type of volatile memory now known or to be developed in the future. Examples include dynamic type random access memory (RAM) or static type RAM. Typically, the volatile memory is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

PERSISTENT STORAGE 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface type operating systems that employ a kernel. The code included in block 210 typically includes at least some of the computer code involved in performing the inventive methods.

PERIPHERAL DEVICE SET 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made though local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

NETWORK MODULE 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

END USER DEVICE (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

REMOTE SERVER 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

PUBLIC CLOUD 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

PRIVATE CLOUD 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

In computing environment 100, an EUD 103 is shown. However, in some embodiments, computer 101 is a user device and a separate EUD 103 is not necessary, as the user interacts directly with computer 101 using, for example, one or more devices in peripheral device set 114. For example, computer 101 may be a user's smart phone and the user may interact with the smart phone using a graphical user interface displayed on a touchscreen.

Referring now to FIG. 2, a second example computing environment 200 for user sensor data labeling is depicted, according to embodiments. Computing environment 200 includes user device 201, wearable device 240, and training system 260. User device 201 may be, for example, a smart phone or other mobile computing device. User device 201 may be connected physically or wirelessly with wearable device 240. User device 201 may communicate with training system 260 via WAN 102.

User device 201 includes user sensor data labeling module 210, GPS receiver 220, and one or more sensors 230. User sensor data labeling module 210 includes a location module 212, evaluation identification module 214, evaluation result module 216, and labeling module 218. User sensor data labeling module 210 may be configured to perform some or all of method 300 described in reference to FIG. 3. Location module 212 may be configured to determine whether the user is at a medical facility using, for example, GPS Receiver 220. Evaluation identification module 214 may be configured to identify when the user is potentially undergoing a medical evaluation, using, for example, sensors 230 and sensors 242. Evaluation result module 216 may be configured to identify results from medical evaluations of the user. Labeling module 218 may be configured to label user sensor data corresponding to the medical evaluations with the identified results and communicate the labeled data to training system 260.

Training system 260 includes a database 270 and machine learning module 280. Database 270 may contain training data 274, including labeled user sensor data 278 received from user devices such as user device 201. Machine learning module 280 may be configured to apply one or more machine learning algorithms to generating or updating models based on the training data 274.

Computing environment 200 may be implemented in computing environment 100. In some embodiments, user device 201 and wearable device 240 may be part of computer 101, with wearable device 240 part of peripheral device set 114, and training system 260 may be remote server 104 and database 270 may be remote database 130.

Figure 3:
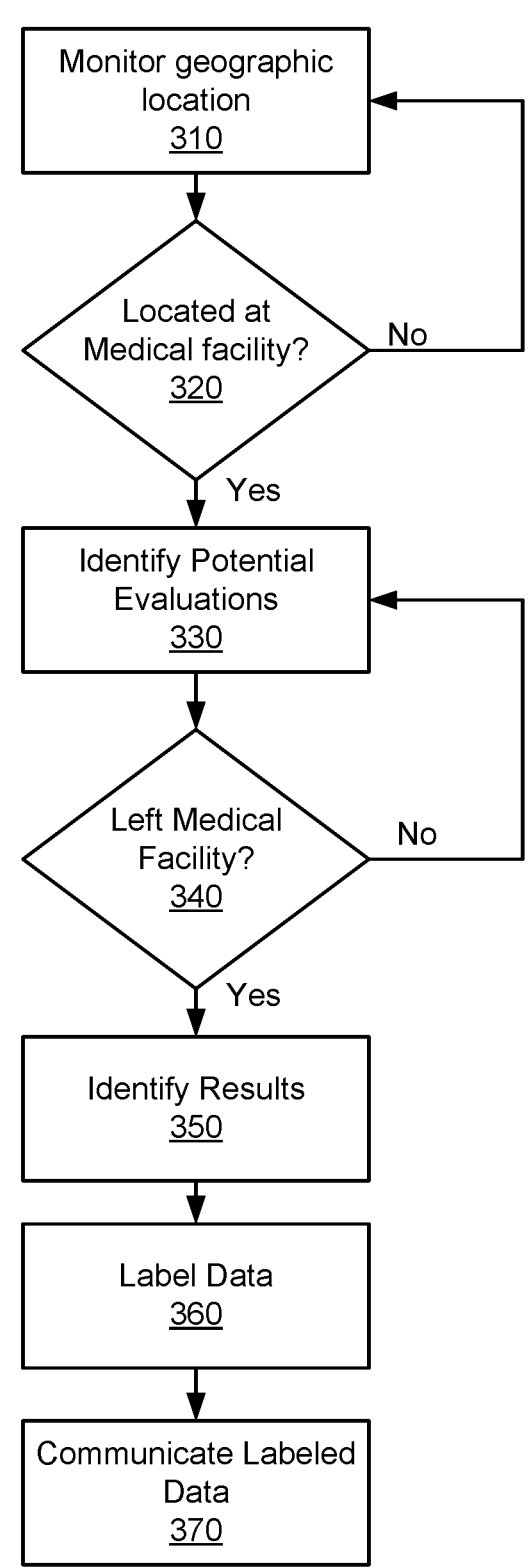
FIG. 3 depicts an example method for automatically labeling user sensor data for machine learning, according to embodiments.

Referring now to FIG. 3, a flow diagram of an example method 300 for automatically labeling user sensor data for machine learning is depicted. Method 300 may be performed by, for example, computer 101 or user device 201. At operation 310, the system monitors the geographic location of a user. The geographic location of the user may be determined using the geographic location of a user device. The geographic location of the user device may be determined using any suitable technology including, for example, GPS, WiFi positioning, etc. For example, location module 212 may obtain the geographic coordinates of user device 201 using GPS receiver 220. According to various embodiments, the location of the user may be checked continuously, intermittently, or periodically.

At operation 320, the system uses the location of the user to determine if the user is located at a medical facility. The location of the user may be compared with known locations of medical facilities. In some embodiments, the location of the user may be overlaid on a geographic information system (GIS) to determine if the user location corresponds to the location of a medical facility. For example, location module 212 may overlay the coordinates obtained from GPS receiver 220 on a GIS to determine if the user device 201 is within a medical facility. If, at operation 320, the system determines that the user is not at a medical facility, the system continues to monitor the location of the user at operation 310. If, at operation 320, the system determines that the user is at a medical facility, the system proceeds to operation 330.

At operation 330, the system identifies periods of time during which potential evaluations are being performed. As used herein, a medical evaluation may be an evaluation using any combination of electronic and medical professional evaluation. In some embodiments, the evaluation may be entirely electronic such as an evaluation using medical-grade electronic sensors and automated determinations using the medical-grade sensor data. In some embodiments, the evaluation may be performed solely based on an evaluation of a medical professional. For example, the medical professional may make a diagnosis based on a physical examination of the user. In further embodiments, the medical evaluation may be based on a combination of both electronic and medical professional evaluation. For example, the user may be evaluated using one or more sensors and a physical evaluation by a medical professional.

In some embodiments, at operation 330, the system may begin collecting user sensor data of one or more sensors from user devices in response to the determination that the user is at the medical facility. The system may utilize data from the one or more sensors and/or the location of the user in identifying periods of time during which potential evaluations are being performed. In some embodiments, the system may compare data from the one or more sensors to one or more profiles associated with a particular type of evaluation to identify a match. A profile may contain an expected result of sensor data from one or more sensors that would be expected when a user is undergoing a specific evaluation. For example, a profile for a pronation-supination (PS) test may include a sample of sensor data from a gyroscope of a smart watch that would be expected from the gyroscope when a user is performing the repeated motions associated with the PS test. The system may compare the similarity between the collected user sensor data with one or more profiles and identify a match if the similarity exceeds a predetermined threshold level. In response to identifying a potential evaluation, the system may record certain information about the evaluation. For example, the system may record the type of evaluation and the start and stop time of the potential evaluation based on the comparison of the user sensor data to the corresponding profile.

In some embodiments, instead of identifying periods of time associated with particular evaluations, the system may identify periods of time when evaluations are more likely to be occurring. For example, the system may be configured to identify periods of time when the user is walking, using sensor and/or geographic location data, as periods of time when the user is likely not undergoing an evaluation, and periods of time when the user is not walking as periods when a user is more likely to be undergoing an evaluation. Similarly, depending on the types of evaluations, the system may be configured to determine that a user may be more likely to be undergoing an evaluation at a period of time if they are determined to be sitting or lying down as determined based on user sensor data.

In response to identifying periods of time that one or more potential evaluations has occurred, is occurring, or is more likely to have occurred, the system may be configured to perform one or more actions on the user sensor data from one or more sensors associated with user devices during the identified time periods. In some embodiments, the user sensor data may be streamed to a cloud storage. In embodiments where user sensor data is stored in a temporary memory, the sensor data collected during the identified periods of time may be copied to a different memory device for longer-term storage. For example, the sensor data may be initially stored in volatile memory 112 and the sensor data collected during the identified periods of time may be copied into persistent storage 113. In some embodiments, metadata may be stored that indicates that the user sensor data during the identified time period may be associated with a medical evaluation. In some embodiments, the metadata may indicate a particular type of evaluation such as, for example, when the time period was identified based on a match between user sensor data and a profile associated with the particular type of evaluation.

For example, evaluation identification module 214 may identify a match between user sensor data from sensors 230 and sensors 242 for a period of time and a profile for a PS test. In response, the evaluation identification module may copy the user sensor data from a volatile memory to a nonvolatile memory and store metadata indicating that the user sensor data may be associated with a PS test.

At operation 340, the system uses the location of the user to determine if the user has left the medical facility. This may be determined in the same way as the system determines if the user is located at a medical facility in operation 320. The location of the user may be compared with the location of the medical facility. In some embodiments, the location of the user may be overlayed on a geographic information system (GIS) to determine if the user location corresponds to the location of the medical facility. For example, location module 212 may overlay the coordinates obtained from GPS receiver 220 on a GIS to determine if the user device 201 is still within a medical facility. If, at operation 340, the system determines that the user is still at the medical facility, the system continues to identify potential evaluations at operation 330. If, at operation 340, the system determines that the user has left the medical facility, the system proceeds to operation 350.

At operation 350, the system determines one or more medical evaluation results for one or more medical evaluations that occurred while the user was at the medical facility. As used herein, a medical evaluation result may be a result from any combination of electronic or medical professional result of an evaluation. In some embodiments, the result may be an electronic result determined, for example, by processing medical-grade sensor data by one or more algorithms to provide a result. In some embodiments, the medical evaluation result may be a determination by a medical professional, alone or in combination with an electronic determination using medical-grade sensors.

In response to determining that the user is no longer at the medical facility, evaluation result module 216 may provide a questionnaire to the user. The questionnaire may be provided to a user via a graphical user interface and may contain one or more selectable objects, lists of selectable options, text boxes, or any other suitable user interface option for a user to input responses to questions in the questionnaire. The questionnaire may ask the user to provide one or more evaluations that occurred at the medical facility and associated evaluation results. For example, evaluation result module 216 may be configured to present a questionnaire on a graphical user interface for the user to select and/or type one or more answers. When a user's sensor data matches a profile for a specific evaluation, the questionnaire may reference the specific evaluation. The questionnaire may further ask the user to provide time periods for the evaluations to better match the evaluations to the corresponding user sensor data. In some embodiments, the questionnaire may request user permission to access the user's electronic medical records to retrieve evaluations and/or evaluation results. For example, evaluation result module 216 may be configured to present a request on a graphical user interface of the user's device that requests access to the user's electronic medical records, with selectable options to grant or deny the request.

At operation 360, one or more sets of user sensor data are labeled using the identified results of one or more medical evaluations of the user. A label indicating the result of a medical evaluation may be applied to a set of user sensor data corresponding to a period of time associated with the evaluation. For example, labeling module 218 may apply a label to a set of user sensor data corresponding to each result identified by evaluation result module 216. In some embodiments, the set of user sensor data may include sensor data from more than one sensor. The set of sensor data may include the data from specific sensors based on the particular evaluation and/or evaluation result. For example, the system may be configured to identify data from specific sensors based on the particular evaluation or evaluation result. When multiple evaluations and/or results are identified, multiple sets of user sensor data may be labeled.

Examples of user sensor data and corresponding results of medical evaluations include:

1) Smart watch, smart ring heart rhythm data:Doctor's diagnosis of atrial fibrillation based on EKG;
2) Heart rate, respiration rate, blood oxygen from smart watch, smart ring, or other sleep monitor:Sleep apnea diagnosis based on Polysomnography;
3) Mobility monitor with wearable inertial sensors (accelerometer, gyroscope):Movement disorder diagnosis based on in-clinic tests;
4) Human pose estimation based on video:Movement disorder diagnosis.

At operation 370, the system communicates the labeled data. The labeled data may be communicated to another system that is associated with training models for evaluating user sensor data and/or storing training data for training such models. For example, labeling module 218 may be configured to communicate one or more sets of labeled user sensor data to training system 260 for storage with training data 274 in database 270.

A specific example implementation according to embodiments of the present disclosure will now be described. Parkinson's disease motor symptoms like bradykinesia (i.e., slowness of movement) are typically assessed in a medical clinic by a trained physician using standardize tests described in UPDRS part III (Unified Parkinson's Disease Rating Scale). During one of these tests, the patient is asked to extend their arm out in front of their body with their palms down, and then to turn their palm up and down, alternately, 10 times as fast and as fully as possible. The physician then scores the test on a scale from 0 to 4 according to the following guideline:

0: Normal: No problems.
1: Slight: Any of the following: a) the regular rhythm is broken with one or two interruptions or hesitations of the movement; b) slight slowing; c) the amplitude decrements near the end of the sequence.

2: Mild: Any of the following: a) 3 to 5 interruptions during the movements; b) mild slowing; c) the amplitude decrements midway in the sequence.
3: Moderate: Any of the following: a) more than 5 interruptions during the movement or at least one longer arrest (freeze) in ongoing movement; b) moderate slowing; c) the amplitude decrements starting after the 1st supination-pronation sequence.
4: Severe: Cannot or can only barely perform the task because of slowing, interruptions, or decrements.

This test is also called the pronation-supination (PS) test and can be easily performed by the patient at home, while wearing a smartwatch or holding a phone with the hand that is doing the movement. Data from 30 subjects conducting such movements was collected as part of a clinical trial and used to develop a model that automatically scores the PS test based on the data from the gyroscope sensor of the smartwatch or smartphone, and the score assigned by the observing physician. However, 30 subjects is a relatively small sample, especially if the models used are deep neural networks. However, this is a typical sample size for clinical trials in the digital health space, because the costs for running a clinical trial are so high.

Embodiments of the present disclosure may allow for the collection of labeled gyroscope data from user's visits to clinics. In particular, gyroscope data may be labeled based on a PS score assigned by a physician. In this example, the user owns a smartwatch that can score PS tests using the model described above. An application on the user's smartwatch is configured to cause the smartwatch to perform method 300 to label gyroscope data from the smartwatch using PS scores assigned by a physician.

At operation 310, the smartwatch monitors the location of the user using a GPS receiver on the smartwatch. The user enters a medical clinic and, at operation 320, the smartwatch determines that the GPS location of the smartwatch is at the medical clinic by, for example, comparing the GPS location to locations of known medical clinics. While the user is at a medical clinic and undergoing a UPDRS test under the supervision of a physician, who also scores the test, at operation 330 the smartwatch monitors gyroscope data from the gyroscope of the smartwatch and identifies a match with expected gyroscope data for a PS test and communicates the gyroscope data to a cloud storage. The user leaves the medical clinic, and, at operation 340, the smartwatch determines that the user is no longer at the medical clinic based on the GPS location of the smartwatch. In response, at operation 350, the smartwatch displays an interface that asks the user to enter the PS score for the PS test. The display contains selectable interface elements for each PS score value. The display also contains a selectable element that indicates that the user does not know the PS score. In response to the user selecting the element indicating that the user does not know the PS score, the smartwatch displays a prompt requesting permission to access the PS score from the user's electronic medical records. In response to the user granting permission to obtain the PS score from the user's electronic medical records, the smartwatch obtains the PS score via an API call to a medical records system containing the user's electronic medical records. At operation 360, the smartwatch communicates the PS score to the cloud storage to label the gyroscope data with the PS score. At operation 370, the gyroscope data labeled with the PS score is communicated to a system that trains and/or updates the model used to automatically score a PS test using gyroscope data.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method comprising:
obtaining Global Positioning System (GPS) coordinates of a user device via a GPS receiver of the user device;
determining, by the user device, that a user is at a medical facility using the GPS coordinates of the user device;
in response to determining that the user is at the medical facility, collecting user sensor data from one or more sensors of a wearable device of the user while the user is at the medical facility, wherein a model associated with the wearable device is configured to make one or more determinations based on the user sensor data;
in response to determining that the user has left the medical facility, retrieving a result of a medical evaluation of the user performed at the medical facility;
labeling user sensor data collected from the wearable device of the user during the medical evaluation with the retrieved result from the medical evaluation; and
communicating the labeled user sensor data to a model training system to update the model.

2. The method of claim 1, wherein determining that the user is at the medical facility comprises:
applying the GPS coordinates to a geographic information system.

3. The method of claim 1, further comprising identifying the medical evaluation and a period of time associated with the medical evaluation based on the collected sensor data by comparing the collected user sensor data to one or more profiles associated with medical evaluations, wherein the labeling user sensor data comprises labeling a set of the user sensor data from the period of time with the result from the medical evaluation.

4. The method of claim 1, wherein retrieving the result of the medical evaluation comprises displaying, on a graphical user interface of the user device, a prompt to enter the result of the medical evaluation.

5. The method of claim 1, wherein retrieving the result of the medical evaluation comprises:
prompting the user for permission to access the user's electronic medical records; and
in response to receiving permission from the user, retrieving the result from the user's electronic medical records via an API call to a medical records system.

6. A system comprising:
one or more processors; and
one or more computer readable storage media storing program instructions executable by the one or more processors to perform operations comprising:
obtaining Global Positioning System (GPS) coordinates of a user device via a GPS receiver of the user device;
determining, by the user device, that a user is at a medical facility using the GPS coordinates of the user device;
in response to determining that the user is at the medical facility, collecting user sensor data from one or more sensors of a wearable device of the user while the user is at the medical facility, wherein a model associated with the wearable device is configured to make one or more determinations based on the user sensor data;
in response to determining that the user has left the medical facility, retrieving a result of a medical evaluation of the user performed at the medical facility; and
labeling user sensor data collected from the wearable device of the user during the medical evaluation with the retrieved result from the medical evaluation; and
communicating the labeled user sensor data to a model training system to update the model.

7. The system of claim 6, wherein determining that the user is at the medical facility comprises:
applying the GPS coordinates to a geographic information system.

8. The system of claim 6, wherein the operations further comprise identifying the medical evaluation and a period of time associated with the medical evaluation based on the collected sensor data by comparing the collected user sensor data to one or more profiles associated with medical evaluations, wherein the labeling user sensor data comprises labeling a set of the user sensor data from the period of time with the result from the medical evaluation.

9. The system of claim 6, wherein retrieving the result of the medical evaluation comprises displaying, on a graphical user interface of the user device, a prompt to enter the result of the medical evaluation.

10. The system of claim 6, wherein retrieving the result of the medical evaluation comprises:
prompting the user for permission to access the user's electronic medical records; and
in response to receiving permission from the user, retrieving the result from the user's electronic medical records via an API call to a medical records system.

11. A computer program product comprising one or more computer readable storage media having program instructions embodied therewith, the program instructions executable by one or more processors to perform operations comprising:
obtaining Global Positioning System (GPS) coordinates of a user device via a GPS receiver of the user device;
determining, by the user device, that a user is at a medical facility using the GPS coordinates of the user device;
in response to determining that the user is at the medical facility, collecting user sensor data from one or more sensors of a wearable device of the user while the user is at the medical facility, wherein a model associated with the wearable device is configured to make one or more determinations based on the user sensor data;
in response to determining that the user has left the medical facility, retrieving a result of a medical evaluation of the user performed at the medical facility;
labeling user sensor data collected from the wearable device of the user during the medical evaluation with the retrieved result from the medical evaluation; and
communicating the labeled user sensor data to a model training system to update the model.

12. The computer program product of claim 11, wherein determining that the user is at the medical facility comprises:
applying the GPS coordinates to a geographic information system.

13. The computer program product of claim 11, wherein the operations further comprise identifying the medical evaluation and a period of time associated with the medical evaluation based on the collected sensor data by comparing the collected user sensor data to one or more profiles associated with medical evaluations, wherein the labeling user sensor data comprises labeling a set of the user sensor data from the period of time with the result from the medical evaluation.

14. The computer program product of claim 11, wherein retrieving the result of the medical evaluation comprises displaying, on a graphical user interface of the user device, a prompt to enter the result of the medical evaluation.

15. The computer program product of claim 11, wherein retrieving the result of the medical evaluation comprises:

prompting the user for permission to access the user's electronic medical records; and in response to receiving permission from the user, retrieving the result from the user's electronic medical records via an API call to a medical records system.

* * * * *